United States Patent

Rayudu et al.

Patent Number: 5,466,717
Date of Patent: Nov. 14, 1995

[54] HALOGENATED 4'-METHOXYACETOPHENONES AS MICROBICIDES AND PRESERVATIVES

[75] Inventors: S. Rao Rayudu; Joseph G. Fenyes, both of Germantown; Thomas E. McNeel, Memphis, all of Tenn.

[73] Assignee: Buckman Laboratories Int'l, Inc., Memphis, Tenn.

[21] Appl. No.: 166,907

[22] Filed: Dec. 15, 1993

Related U.S. Application Data

[63] Continuation of Ser. No. 879,982, May 8, 1992, abandoned.

[51] Int. Cl.⁶ .......................... A01N 31/14; A01N 35/00; A61K 31/12
[52] U.S. Cl. ................................. 514/689; 504/161
[58] Field of Search .................. 514/688, 689; 504/161

[56] References Cited

U.S. PATENT DOCUMENTS

| | | | |
|---|---|---|---|
| Re. 26,178 | 3/1967 | Lukes et al. | 514/689 |
| 2,881,070 | 4/1959 | Pera | 92/3 |
| 3,021,256 | 2/1962 | Hollenback et al. | 162/161 |
| 3,184,379 | 5/1965 | Lukes et al. | 514/689 |
| 3,354,033 | 11/1967 | Buckman et al. | 162/161 |

FOREIGN PATENT DOCUMENTS

209716 5/1984 German Dem. Rep. .

*Primary Examiner*—Allen J. Robinson
*Attorney, Agent, or Firm*—Finnegan, Henderson, Farabow, Garrett & Dunner

[57] ABSTRACT

Halogenated 4'-methoxyacetophenones of formula I:

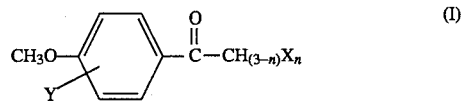

wherein X is a halogen; Y is a halogen; and n is 1 or 2 as microbicides for inhibiting the growth of microorganisms in aqueous systems and on surfaces, as well as for inhibiting slime formation in aqueous systems and biocidal compositions containing effective amounts of the halogenated 4'-methoxyacetophenones.

27 Claims, No Drawings

HALOGENATED 4'-METHOXYACETOPHENONES AS MICROBICIDES AND PRESERVATIVES

This application is a continuation of application Ser. No. 07/879,982 filed May 8, 1992, now abandoned.

BACKGROUND OF THE INVENTION

The present invention relates to the use of halogenated 4'-methoxyacetophenones, such as 2,3'-dihalo-4'-methoxyacetophenones and 2,2,3'-trihalo-4'-methoxyacetophenones, as microbicides and preservatives.

A large number of commercial, industrial, agricultural and wood products are subject to microbiological attack which reduces or destroys their economic value. These products often contain relatively large amounts of water. Examples of materials that are subject to degradation are surface coatings, wood, agricultural seed, leather, fabrics and plastics (including flexible plastics). Examples of products sold as aqueous systems which are subject to attack are latexes, surfactants, dispersants, stabilizers, thickeners, adhesives, starches, waxes, proteins, emulsifying agents, detergents, cellulose products, and resins. These aqueous-based products generally contain organic material and are formulated in aqueous solutions, emulsions or suspensions. Specific aqueous-based products are water-based paints and metalworking fluids.

The temperature at which these products are stored and their intrinsic characteristics make them susceptible to the growth of microorganisms. These microorganisms can be introduced during the manufacturing of a product by exposure to air, tanks, pipes, equipment, and humans; and/or during the use of a product from multiple openings and reclosures of packaged products; or by the introduction of contaminated objects to stir or remove material.

Microbiological degradation of aqueous systems containing organic materials may manifest itself in a variety of problems, such as loss of viscosity, gas formation, objectionable odors, decreased pH, emulsion breaking, color change, and gelling. This degradation often renders the system ineffective for its desired use.

Another objectionable phenomenon occurring in industrial process systems involving water is slime formation. Slime consists of matted deposits of microorganisms, fibers and debris. It may be stringy, pasty, rubbery, tapioca-like, or hard; and may have a characteristic odor that is different from that of the liquid suspensions in which it is formed. Primarily, the microorganisms involved in slime formation are different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeasts, and yeast-like organisms. Slime reduces yields in industrial processes, such as paper production, and causes plugging and other problems in water systems.

Compounds containing brominated acetophenones are known in the literature as microbicides. For example, U.S. Pat. No. 3,354,033 describes the use of 2-bromoacetophenones as slime controlling agents. East German Patent DD 209,716 describes some of the 2,2-dihaloacetophenones as fungicides. However, the microbicidal properties of acetophenone derivatives having a methoxy group in the 4'-ring position, a halogen at another ring position and a halogenated acetyl group in the 1-position have not been described in the literature.

SUMMARY OF THE INVENTION

One object of the present invention is to inhibit the growth of microorganisms in an aqueous system. A second object is to inhibit slime formation in an aqueous system. A third object is to inhibit the growth of microorganisms on a substance or surface susceptible to deterioration by microorganisms.

These objects are accomplished by employing a halogenated 4'-methoxyacetophenone of formula I:

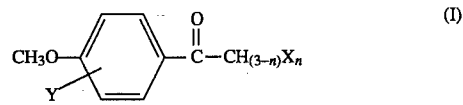

wherein
  X is a halogen;
  Y is a halogen; and
  n is 1 or 2;
in one of the following methods:
  a method for inhibiting the growth of microorganisms in an aqueous system comprising the step of adding to an aqueous system a halogenated 4'-methoxyacetophenone of formula I in an amount effective to inhibit the growth of at least one microorganism;
  a method for inhibiting slime formation in an aqueous system comprising the step of adding to an aqueous system a halogenated 4'-methoxyacetophenone of formula I in an amount effective to inhibit the growth of slime; and
  a method for inhibiting the growth of microorganisms on a substance comprising the step of applying to a substance a halogenated 4'-methoxyacetophenone of formula I in an amount effective to inhibit the growth of at least one microorganism.

The objects of the invention are also accomplished with a biocidal composition comprising an effective amount of a halogenated 4'-methoxyacetophenone of formula I and an organic solvent.

Additional objects and advantages of the invention will be set forth in the description which follows, and in part will be apparent from the description, or may be learned by practice of the invention. The objects and advantages of the invention may be realized and obtained by means of the combinations particularly pointed out in the appended claims.

DETAILED DESCRIPTION OF THE INVENTION

Halogenated 4'-methoxyacetophenones can be prepared by using methods described in the literature. For example, Karl W. Rosemund and Klaus Pfroepffer, Chem. Ber. 90, 1922-8 (1957) describes the preparation of 2,2,3'-tribromo-4'-methoxyacetophenone by treating 4'-methoxyacetophenone with bromine in chloroform. Other halogenated 4'-methoxyacetophenones are prepared by starting with 4'-methoxyacetophenone, halogenating at a ring position, and then following the literature methods to affect the desired halogenation on the acetyl side chain. As would be understood by one of ordinary skill, any equivalent method which yields the desired end product may be used.

As described below the compounds employed in the present invention are halogenated 4'-methoxyacetophenones of the formula I:

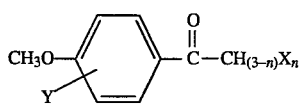

$$\text{CH}_3\text{O}-\underset{Y}{\underset{|}{\diagdown}}\overset{}{\bigcirc}-\overset{\overset{O}{\|}}{C}-\text{CH}_{(3-n)}X_n \quad \text{(I)}$$

where X is a halogen; n is 1 or 2; and Y is a halogen. Preferably, X and Y are each selected from chlorine, bromine and iodine. Examples of halogenated 4'-methoxyacetophenones of formula I employed in the present invention are:

2,3'-dichloro-4'-methoxyacetophenone;
2,3'-dibromo-4'-methoxyacetophenone;
2,3'-diiodo-4'-methoxyacetophenone; .
2-bromo,3'-chloro-4'-methoxyacetophenone;
2-chloro,3'-bromo-4'-methoxyacetophenone;
2-chloro,3'-iodo-4'-methoxyacetophenone;
2-bromo,3'-iodo-4'-methoxyacetophenone;
2-iodo,3'-chloro-4'-methoxyacetophenone;
2,2,3'-trichloro-4'-methoxyacetophenone;
2,2,3'-tribromo-4'-methoxyacetophenone;
2,2,3'-triiodo-4'-methoxyacetophenone;
2,2-dichloro,3'-bromo-4'-methoxyacetophenone;
2,2-dibromo,3'-chloro-4'-methoxyacetophenone;
2,2-dibromo,3'-iodo-4'-methoxyacetophenone; and
2,2-dichloro,3'-iodo-4'-methoxyacetophenone.

Of the compounds of formula I, 2,3'-dibromo-4'-methoxyacetophenone and 2,2,3'-tribromo-4'-methoxyacetophenone are preferred compounds to be used according to the present invention.

It has been found that halogenated 4'-methoxyacetophenones are useful for inhibiting the growth of microorganisms in aqueous systems. Thus, the present invention relates to a method of inhibiting the growth of at least one microorganism in an aqueous system comprising the step of adding to an aqueous system a halogenated 4'-methoxyacetophenone in an amount effective to inhibit the growth of at least one microorganism. Representative aqueous systems include aqueous solutions, emulsions and suspensions as described above. Specific systems include water-based paints and metalworking fluids.

Halogenated 4'-methoxyacetophenones have also been found to be useful for inhibiting the formation of slime in an aqueous system. The present invention, then, also relates to a method for inhibiting the formation of slime in aqueous systems comprising the step of adding to an aqueous system a halogenated 4'-methoxyacetophenone in an amount effective to inhibit the formation of slime. This method is effective in aqueous systems such as a pulp slurry or liquids used in a water cooling device.

A further use of halogenated 4'-methoxyacetophenones according to the present invention resides in a method for inhibiting the growth of at least one microorganism on a substance susceptible to deterioration or disfigurement by microorganisms or metabolic products of microorganisms. The method comprises the step of applying or admixing with the substance the halogenated 4'-methoxyacetophenone in an amount effective to inhibit the growth of at least one microorganism. This method is effective on substances such as wood, surface coatings (i.e. paint films), leather, fabrics, agricultural seed, man-made or naturally occurring polymers (including flexible plastic) and the like. This method of inhibiting the growth of microorganisms on surfaces achieves the desired inhibition for long periods of time, even up to or for more than five years. The microorganisms whose growth is inhibited include fungi.

The present invention also relates to biocidal compositions comprising an effective amount of a halogenated 4'-methoxyacetophenone of formula I and an organic solvent. The biocidal composition can contain other additives such as surfactants, defoamers, and emulsifiers as are known in the art. A biocidal-composition containing a halogenated 4'-methoxyacetophenone can be used in any of the methods described above.

According to the present invention, inhibition of the growth of at least one microorganism or of slime formation encompasses both the prevention and/or reduction of that growth or formation. Therefore, for example, the inhibition of the growth of at least one microorganism in an aqueous fluid can be achieved by preventing such growth in the first instance, preventing further growth if such has already occurred, and/or reducing the amount of any existing growth.

The use of halogenated 4'-methoxyacetophenones as microbicides has a number of advantages over the microbicides hitherto available. The compounds are excellent microbicides to be used for both preservation of paint while in its container, as well as, after application on a painted surface. They are hydrolyrically stable over a wide pH range (3–11) and can be used in both latex and oil-based systems. They are soluble in many solvents and therefore may be readily diluted for convenience of use. Their compatibility, low color, and efficiency makes them advantageous for use as microbicides in man-made or naturally occurring polymers and for impregnation in or application on surfaces such as wood, paper, or other materials.

The halogenated 4'-methoxyacetophenones may, of course, be applied in various ways—incorporated into a coating or composition, applied as dust by mixing with powdered diluents, dissolved in a solvent, or emulsified into water and then dispersed into a non-solvent. The particular use desired will generally dictate the method of application.

The effective amount or percentage of active compound necessary to achieve the desired result will vary somewhat depending on the substrate to be protected, the conditions for algal bacterial or fungal growth, and the degree of protection desired. For the treatment of surfaces or materials, the concentration of a halogenated 4'-methoxyacetophenone according to the present invention generally ranges from about 0.0001% to 4% (w/w); preferably 0.0001% to 0.2%, and more preferably 0.0005% to 0.005% in the composition applied. With aqueous systems, a preferred effective amount of active compound ranges from 20 to 5000 parts per million, and more preferably, from 250 to 2000 parts per million of the aqueous system. The amount of halogenated 4'-methoxyacetophenone effective to prevent the formation of slime in an aqueous liquid preferably ranges from 1 to 200 parts per million, and more preferably, from 5 to 25 parts per million of the aqueous liquid.

To illustrate the nature of the invention, the following examples are given. It should be understood, however, that the invention is not to be limited to the specific conditions or details set forth in these examples. In the examples, preferred compounds 2,3'-dibromo-4'-methoxyacetophenone and 2,2,3' -tribromo-4'-methoxyacetophenone are abbreviated as compounds 1 and 2, respectively.

EXAMPLE 1

The preservative effectiveness of compounds 1 and 2 was determined in a freshly prepared water-based paint formulated with titanium dioxide and calcium carbonate as pigments, an acrylic resin emulsion, dispersants, and hydroxyethyl cellulose as a thickener. The pH of this paint was approximately 9.0. The test was conducted as follows:

Compounds 1 and 2 were individually added to separate completed acrylic latex paints at levels ranging from 250 to 2000 parts per million parts of the paint. One hundred gram samples of the test paints were challenged initially and at the end of the third and sixth weeks in a three-challenge, nine-week test with 1.0 milliliter of paint containing *Pseudomonas aeruginosa*, *Enterobacter serogenes* and *Bacillus subtilus* at a level of approximately $1.5 \times 10^6$ organisms per milliliter. After vigorous shaking, the inoculated paint was incubated at 28° C. Growth in system was monitored by streaking a sample of each test paint onto a nutrient agar on plates at intervals of 1 day, 2 days, 3 days, 7 days, and 21 days after each challenge. The streaked plates were incubated at 37° C. and examined for bacterial growth after 24 hours (challenge 1). A second sample of the same inoculated paint was rechallenged at the end of 21 days (challenge 2) and again at the end of 42 days (challenge 3). The results obtained are shown in Table 1. A rating of "0" indicates that no growth was observed, "+" indicates that less than 10 colonies were observed, and "++" indicates that 10 or more colonies were observed.

TABLE 1

Results of 9 week multiple challenge test on preservation of the latex paint with compounds listed below. Observation of growth 21 days after challenge.

| Preservative | Challenge Number | | |
|---|---|---|---|
| (ppm, w/w) | 1 | 2 | 3 |
| Compound 1 | | | |
| 5000 | 0 | 0 | 0 |
| 2500 | 0 | 0 | 0 |
| 500 | 0 | 0 | 0 |
| 250 | 0 | 0 | 0 |
| 100 | ++ | ++ | ++ |
| Compound 2 | | | |
| 5000 | 0 | 0 | 0 |
| 2500 | 0 | 0 | 0 |
| 500 | 0 | 0 | 0 |
| 250 | 0 | 0 | 0 |
| 100 | ++ | ++ | ++ |
| Control with no biocide | ++ | ++ | ++ |

EXAMPLE 2

Compounds 1 and 2 were tested by the pulp substrate method described in detail in U.S. Pat. No. 2,881,070, column 5, line 12—column 6, line 53. The disclosure of U.S. Pat. No. 2,881,070 is specifically incorporated here by reference. As set forth in that test method, a percentage kill of 80% or higher represents an extremely useful composition, and it does not follow that higher kills are necessarily better or more desirable. The tests utilized *Enterobacter aerogenes* and *Pseudomonas aeruginosa* in pulp substrates that had been buffered at pH 7.0 and 8.0. The results are presented in Table 2.

TABLE 2

Percent kill of *Enterobacter aerogenes* and *Pseudomonas aeruginosa* in a pulp substrate at pH 7.0 and 8.0 after hours of contact with compounds 1 and 2.

| Concentration | % Kill of E. aerugenes | | % Kill of P. aeroginosa | |
|---|---|---|---|---|
| (ppm) | pH 7.0 | pH 8.0 | pH 7.0 | pH 8.0 |
| Compound 1 | | | | |
| 1 | 31 | 73 | 6 | 85 |
| 2 | 25 | 81 | 7 | 75 |
| 4 | 38 | 93 | 43 | 89 |
| 8 | 0 | 97 | 67 | 70 |
| 10 | 10 | 92 | 93 | 79 |
| 15 | 18 | 99.8 | 94 | 94 |
| 20 | 96 | 100 | 98 | 89 |
| 25 | 99 | 97.8 | 97 | 99 |
| Compound 2 | | | | |
| 1 | 12 | 9 | 15 | 0 |
| 2 | 22 | 43 | 0 | 54 |
| 4 | 41 | 83 | 36 | 25 |
| 8 | 35 | 91 | 17 | 71 |
| 10 | 39 | 89 | 80 | 86 |
| 15 | 52 | 96 | 97 | 94 |
| 20 | 45 | 98 | 98 | 99 |
| 25 | 51 | 99 | 97 | 99 |

As can be seen from the above table, compounds 1 and 2 are good bactericides at both neutral and alkaline pH.

EXAMPLE 3

The growth inhibiting activity of compounds 1 and 2 on the fungus *Aspergillus niger* was evaluated. A variation of the pulp substrate method of Example 2 was used.

When fungi are used as test organisms, the pulp-substrate test method is modified to permit the growth of fungi. The pulp substrate comprises an aqueous slurry of spruce groundwood containing 1 percent by weight (dry basis) of wood fibers enriched by the addition of 0.26 percent of sodium nitrate and 0.64 percent of maltose (technical grade). Forty-gram portions of the enriched groundwood pulp slurry were added to 250 mL Erlenmeyer flasks fitted with loose metal caps and were then sterilized. Each of the following substances was then added to the flasks in the order listed:

(1) Sterile, demineralized water as required in each individual case was added to bring the total weight of the contents of each flask to 50 grams, after allowing for all subsequent additions specified hereinafter (including inoculation with the aqueous suspension of spores and/or mycelial fragments of the test fungus).

(2) One milliliter of a 2.0 percent by weight sterile solution of rosin size. Rosin size is the pasty sodium soap of rosin containing approximately 20 to 30 percent free rosin and 30 percent water. A suitable rosin size is that known as rosin size 70D made by Papermaker's Chemical Department, Hercules, Inc., Kalamazoo, Mich.

(3) A solution of the toxicant or control agent to be evaluated in each test, to give the concentration desired in parts per million by weight.

(4) A sterile solution of buffer salts to adjust the substrate to a pH of 4.5 to 5.0, prepared from 0.2M solutions of potassium acid phthalate and sodium hydroxide. The buffer mixtures were prepared according to the procedures set forth in U.S. Pat. No. 2,881,070.

(5) Inoculum consisting of 1 milliliter of an aqueous suspension of spores and/or mycelial fragments of the test organism, *Aspergillus niger.*

After the inoculant suspensions of the test fungi were added, the flasks were incubated at a temperature of 30°±1° C. for a period adequate for growth to occur in the controls (portions of inoculated pulp substrate which contained no toxicant). The customary periods of incubation were 7 and 14 days. Growth was recorded after each period on the basis of the following key:

4=excellent
3=good
2=poor
1=very poor, scant, questionable
0=no growth

The results are given in Table 3.

TABLE 3

| Inhibition of *Aspergillus niger* by compounds 1 and 2. | |
|---|---|
| Concentration (ppm) | After 14 Days |
| Compound 1 | |
| 5 | 4 |
| 10 | 2 |
| 25 | 0 |
| 100 | 0 |
| Compound 2 | |
| 5 | 4 |
| 10 | 2 |
| 25 | 0 |
| 100 | 0 |

EXAMPLE 4

A standard method to determine the resistance to growth of mold on the surface of interior coatings in an environmental chamber, ASTM method D3273-86, was used to determine the effectiveness of compounds 1 and 2.

Treatments were prepared by dissolving 2.0 g of the compounds of the present invention in 10 mL of acetone/methanol. Two types of paint were used: namely, an alkyd (self-priming white with Beckasol 296-70) and a latex (self-priming, alkyd-modified acrylic paint). To 100-gram samples of each paint was added 2.5, 1.25, 0.625, 0.312 or 0.156 mL to achieve 0.5%, 0.25%, 0.125%, 0.062% or 0.031% active ingredient (w/w), respectively. Each sample was shaken vigorously for 5 minutes using a standard paint shaker.

Blocks of drywall having two inch by four inch dimensions were painted on the front surface and on all edges with two coats of the respective treatments. After drying, the back side was painted with one coat of clear latex. A hole was drilled half-way through the block at one end, and duplicate blocks per treatment were hung in an environmental chamber.

The aggressive nature of the interior of the chamber was developed by inoculating trays of moist potting soil with active cultures of *Aspergillus sp., Aureobasidium sp., Trichoderma sp., Penicillium sp.,* and *Chaetomium sp.* The chamber was maintained at 100 percent relative humidity and 32° C. Final observations were made after four weeks (for latex blocks) or eight weeks (for alkyd blocks).

Subjective scores were assigned based on:

10=no mold growth
9=very slight mold growth
8=slight growth
7,6=slight to medium growth
5=failure (extensive growth)

The results are tabulated in Table 4.

TABLE 4

Growth of mold on the surface of interior coatings preserved with compounds 1 and 2 in an environmental chamber.

| Treatment Level (% by weight) | Latex | Alkyd |
|---|---|---|
| Control | | |
| 0 | 5 | 5 |
| Compound 1 | | |
| 0.01 | 8 | 5 |
| 0.025 | 8 | 5 |
| 0.05 | 9 | 6 |
| 0.10 | 9 | 6 |
| 0.25 | 10 | 7 |
| 0.50 | 10 | 7 |
| Compound 2 | | |
| 0.01 | 9 | 5 |
| 0.025 | 10 | 5 |
| 0.05 | 10 | 6 |
| 0.10 | 10 | 8 |
| 0.25 | 10 | 10 |
| 0.50 | 10 | 10 |

EXAMPLE 5

Compounds 1 and 2 were tested against bacterial growth by the basal salts method described in U.S. Pat. No. 2,881,070, Column 5, line 12—Column 6, line 53. The disclosure of U.S. Patent No. 2,881,070 is specifically incorporated here by reference. As discussed in U.S. Pat. No. 2,881,070, a percentage kill of 80% or higher represents an extremely useful microbicidal composition, but it does not follow that higher kills are necessarily better or more desirable. The results of this test are provided in Table 5.

TABLE 5

| Percentage kill achieved by compounds 1 and 2 in basal salts. | | | | |
|---|---|---|---|---|
| Concentration | *E. aerogenes* | | *P. aeruginosa* | |
| (ppm) | pH 6.0 | pH 8.0 | pH 6.0 | pH 8.0 |
| Compound 1 | | | | |
| 2 | — | 99.0 | — | — |
| 4 | — | 99.9 | — | — |
| 8 | — | 99.99 | — | — |
| 10 | 99.96 | 100 | 99.97 | 98 |
| 20 | 99.96 | 100 | 99.96 | 99 |
| 30 | 100 | 100 | 100 | 99.6 |
| Compound 2 | | | | |
| 2 | — | 57 | — | — |
| 4 | — | 100 | — | — |
| 8 | — | 100 | — | — |
| 10 | 100 | 100 | 99.8 | 94 |
| 20 | 100 | 100 | 100 | 99.96 |
| 30 | 100 | 100 | — | 99.96 |

EXAMPLE 6

The growth-inhibiting activity of the method of the invention against the algae *Chlorella pyrenoidosa* was evaluated at two different pH levels in Difco Algae Broth. The content of the broth was as follows:

| Compound | Grams per liter |
|---|---|
| Sodium nitrate | 1.000 |
| Ammonium chloride | 0.050 |
| Calcium chloride | 0.058 |
| Magnesium sulfate | 0.513 |
| Dipotassium Phosphate | 0.250 |
| Ferric chloride | 0.003 |

Forty-gram portions of the algae medium were added to 250 mL Erlenmeyer flasks fitted with loose metal caps and were then sterilized. Each of the following substances was then added to the flasks in the order listed:

(1) Sterile algae medium as required to bring the total weight of the contents of each flask to 50 grams, after allowing for all subsequent additions specified below.

(2) A solution of the toxicant or of a control agent to be evaluated in each test, to give the concentration desired in parts per million by weight.

(3) *Chlorella pyrenoidosa*, in amounts sufficient to give excellent growth in the controls after 14 days. This was achieved by adding 1 milliliter of a 14 day old culture having luxuriant growth. The *Chlorella pyrenoidosa* culture was obtained from American Type Culture Collection No. 7516.

Control experiments were carried out where no toxicants were employed. In the algicidal tests the growth of algae in the nutrient is lush green and can be seen with the naked eye. Since the minimum inhibitory concentrations of the compounds in this example are those which result in complete inhibition, evaluation of the test results is not subjective.

After the inoculum of the test algae was added, the flasks were incubated at a temperature of 28°±2° C. under fluorescent illumination of 250 foot-candle intensity (8 hours light, 16 hours darkness) for a period adequate for growth in the controls (those portions of medium which contained no toxicant). Observations of growth were made at 7-day intervals. Minimum inhibitory concentrations are those that prevented complete growth after 28 days. The results are summarized in Table 6.

TABLE 6

Minimum inhibitory concentration of compounds 1 and 2 against algae in parts per million

| | C. pyrenoidosa | |
|---|---|---|
| Compound | pH 7.0 | pH 8.0 |
| 1 | 4 | 2 |
| 2 | 8 | 4 |

EXAMPLE 7

The effectiveness of compounds 1 and 2 against *Desulfovibrio desulfuricans*, a sulfate reducing bacterium, was determined using the method recommended by the American Petroleum Institute (Method API Rp 38).

The composition of the sulfate-reducer medium for the bacteriostatic test is as follows:

| Sodium lactate, USP | 4.0 mL |
|---|---|
| Yeast extract, | 1.0 g |
| Ascorbic acid | 0.1 g |
| $MgSO_4 \cdot 7H_2O$ | 0.2 g |
| $K_2HPO_4$ (anhydrous) | 0.01 g |
| $Fe(SO_4)_2(NH_4)_2 \cdot 6H_2O$ (added after sterilization) | 0.2 g |
| NaCl | 10.0 g |
| Distilled water | 1,000.0 mL |

The ingredients are dissolved by gentle heating with constant stirring. After dissolution has occurred, the pH of the medium was adjusted to 7.3 with NaOH. If necessary, the medium is then filtered through Whatman No. 1 or No. 2 filter paper. Following filtration, the medium is autoclaved at 15 lb steam pressure for min. After autoclaving, the medium is allowed to cool slightly and the iron salt, $Fe(SO_4)_2(NH_4)_2 \cdot 6H_2O$, is added. The pH is then checked and readjusted if necessary. The medium is now cooled to room temperature as rapidly as possible, without agitation.

After cooling, the medium is inoculated from the third successive 24-hour transfer of an actively growing culture (a liquid culture which turns black within 24 hours after inoculation) of sulfate-reducing bacteria. Ten milliliters of inoculum are added to each liter of medium.

From stock solutions of the chemical to be screened, sufficient amounts of the compounds are added to 1- or 2-oz clear bottles so that the desired concentrations of chemicals are present when the containers are filled. The amount of stock solution added cannot exceed 10 percent of the volume of the test bottle. After addition of the chemical, the bottles are completely filled with the inoculated medium. The bottles are then capped with plastic caps containing cork and aluminum foil or Teflon liners and are incubated at 30°±2° C.

All work is done in duplicate with at least three controls for each series. The controls consist of bottles filled with inoculated medium only. Growth of sulfate-reducing bacteria in the bottles is indicated by an intense blackening of the medium, whereas containers having sufficient chemical to inhibit growth will remain clear. Bottles with no sulfate-reducing bacteria growth are observed for a period of 28 days after the controls have blackened.

The results were recorded using a +/0 scale where "+" indicates growth and "0" indicates no growth. Results are listed in Table 7.

TABLE 7

Effectiveness of compounds 1 and 2 against *Desulfovibrio desulfuricans* at pH 7.0.

| Concentration (ppm) | Compound 1 | Compound 2 |
|---|---|---|
| 0 | + | + |
| 0 | + | + |
| 1 | + | + |
| 1 | + | + |
| 2 | + | + |
| 2 | + | + |
| 4 | 0 | 0 |
| 4 | 0 | 0 |
| 8 | + | + |
| 8 | + | 0 |
| 10 | 0 | 0 |
| 10 | 0 | 0 |
| 15 | 0 | 0 |
| 15 | 0 | 0 |

TABLE 7-continued

Effectiveness of compounds 1 and 2 against
*Desulfovibrio desulfuricans* at pH 7.0.

| Concentration (ppm) | Compound 1 | Compound 2 |
|---|---|---|
| 20 | 0 | 0 |
| 20 | 0 | 0 |

EXAMPLE 8

The effectiveness of halogenated 4'-methoxyacetophenones were evaluated for long term control of fungal and algal growth on a paint film following ASTM Procedure #D3456 (ASTM, 1916 Race St., Philadelphia, Pa. 19103). The test compared the effectiveness of compound 2, 2,2,3'-tribromo-4'-methoxyacetophenone, in latex paint with the commercially available biocides such as Nopcocide-96, and Troysan Polyphase over a period of 5 years and 5 months. The test paint was brush-applied (2 coats) over Southern yellow pine panels. A minimum of 24 hours was allowed between coats. The panels were rated based on the ASTM Procedure #D3274:

10=no growth

8=slight growth

4=heavy growth

2=very heavy growth

0=full coverage

The results are listed in Table 8.

TABLE 8

Comparison of effectiveness of compound 2 and
commercial biocides in paint film preservation.

| BIOCIDE (Concentration) | ALGAE | FUNGI |
|---|---|---|
| Nopcocide N-96 (0.3%) | 2.0 | 5.0 |
| Compound 2 (0.25%) | 6.0 | 5.0 |
| Compound 2 (0.5%) | 5.0 | 5.0 |
| Troysan Polyphase (0.25%) | 0.0 | 5.0 |

The claimed invention is:

1. A method for inhibiting the growth of a microorganism in an aqueous system comprising the step of adding to said aqueous system a halogenated 4'-methoxyacetophenone of formula I:

$$CH_3O-\underset{Y}{\underset{|}{\bigcirc}}-\overset{O}{\underset{\|}{C}}-CH_{(3-n)}X_n \quad (I)$$

wherein

X is a halogen;

Y is a halogen; and n is 2;

in an amount effective to inhibit the growth of said microorganism.

2. The method of claim 1 wherein the microorganism is selected from the group consisting of bacteria, fungi and algae.

3. The method of claim 1 wherein X is Cl, Br, or I and Y is Cl, Br, or I.

4. The method of claim 3 wherein the halogenated 4'-methoxyacetophenone is 2,2,3'-tribromo-4'-methoxyacetophenone.

5. The method of claim 3 wherein the aqueous system is a paint, coating, metalworking fluid, cooling water system, raw water system, waste water system, paper machine process water system or a cellulose pulp slurry.

6. The method of claim 4 wherein the aqueous system is a paint, coating, metalworking fluid, cooling water system, raw water system, waste water system, paper machine process water system or a cellulose pulp slurry.

7. The method of claim 3 wherein the halogenated 4'-methoxyacetophenone is present in an amount ranging from 1 to 5000 parts per million of the aqueous system.

8. A method for inhibiting slime formation in an aqueous system comprising the step of adding to said aqueous system a halogenated 4'-methoxyacetophenone of formula I:

$$CH_3O-\underset{Y}{\underset{|}{\bigcirc}}-\overset{O}{\underset{\|}{C}}-CH_{(3-n)}X_n \quad (I)$$

wherein

X is a halogen;

Y is a halogen; and n is 2;

in an amount effective to inhibit the growth of slime.

9. The method of claim 8 wherein X is Cl, Br, or I and Y is Cl, Br, or I.

10. The method of claim 9 wherein the halogenated 4'-methoxyacetophenone is 2,2,3'-tribromo-4'-methoxyacetophenone.

11. The method of claim 9 wherein the aqueous system is a metalworking fluid, cooling water system, raw water system, waste water system, or paper machine process water system.

12. The method of claim 10 wherein the aqueous system is a metalworking fluid, cooling water system, raw water system, waste water system, or paper machine process water system.

13. The method of claim 9 wherein the halogenated 4'-methoxyacetophenone is present in an amount ranging from 1 to 200 parts per million of the aqueous system.

14. A method from inhibiting the growth of a microorganism on a substance susceptible to deterioration or disfiguration by the microorganism comprising the step of contacting said substance with a halogenated 4'-methoxyacetophenone of formula I:

$$CH_3O-\underset{Y}{\underset{|}{\bigcirc}}-\overset{O}{\underset{\|}{C}}-CH_{(3-n)}X_n \quad (I)$$

wherein

X is a halogen;

Y is a halogen; and n is 2;

in an amount effective to inhibit the growth of said microorganism on the substance.

15. The method of claim 14 wherein X is Cl, Br, or I and Y is Cl, Br, or I.

16. The method of claim 15 wherein the halogenated 4'-methoxyacetophenone is 2,2,3'-tribromo-4'-methoxyacetophenone.

17. The method of claim 15 wherein said substance is wood, paper, leather, fabric, agricultural seed or plastic.

18. The method of claim 15 wherein said substance is paint or a paint coating.

19. The method of claim 15 wherein a composition containing the halogenated acetophenone is applied to a surface of said substance and the halogenated 4'-methoxyacetophenone is present in an amount ranging from 0.01% to 4% (w/w) of the composition.

20. The method of claim 19 wherein the composition is a paint composition or a coating composition.

21. The method of claim 20 wherein said substance is wood, paper, leather, fabric, or plastic.

22. A microbicidal composition comprising an effective amount of a halogenated 4'-methoxyacetophenone of the formula I:

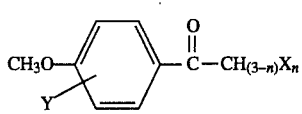

wherein

X is a halogen;

Y is a halogen; and n is 2;

in a solvent.

23. The composition of claim 22 wherein X is Cl, Br, or I and Y is Cl, Br, or I.

24. The composition of claim 23 wherein the halogenated 4'-methoxyacetophenone is 2,2,3'-tribromo-4'-methoxyacetophenone.

25. A method for inhibiting the growth of a microorganism in a cosmetic or pharmaceutical composition comprising the step adding to said composition a halogenated 4'-methoxyacetophenone of formula I:

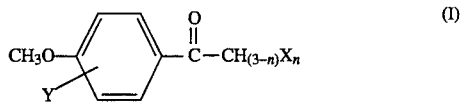

wherein

X is a halogen;

Y is a halogen; and n is 2;

in an amount effective to inhibit the growth of said microorganism.

26. The method of claim 25 wherein X is Cl, Br, or I and Y is Cl, Br, or I.

27. The method of claim 26 wherein the halogenated 4'-methoxyacetophenone is 2,2,3'-tribromo-4'-methoxyacetophenone.

* * * * *

UNITED STATES PATENT AND TRADEMARK OFFICE
CERTIFICATE OF CORRECTION

PATENT NO. : 5,466,717
DATED : November 14, 1995
INVENTOR(S) : S. Rao RAYUDU and Joseph G. FENYES It is certified that error appears in the above-identified patent and that said Letters Patent is hereby corrected as shown below:

Claim 4, Col. 11, lines 65 and 66, there is an improper line break; "4" and " ' " should appear on the same line, and the phrase should read --4'-methoxyacetophenone--.

Signed and Sealed this

Thirtieth Day of January, 1996

*Attest:*

BRUCE LEHMAN

*Attesting Officer*  *Commissioner of Patents and Trademarks*